United States Patent [19]

Sterling et al.

[11] Patent Number: 5,486,541
[45] Date of Patent: Jan. 23, 1996

[54] MONOFLUORINATED DERIVATIVES OF N-PROPARGYL-1-AMINOINDAN AND THEIR USE AS INHIBITORS OF MONOAMINE OXIDASE

[75] Inventors: Jeff Sterling, Jerusalem; Ruth Levy, Tel-Aviv; Alex Veinberg, Rehovot; Willy Goldenberg, Jerusalem; John Finberg, Tivon; Musa Youdim; Arieh Gutman, both of Haifa, all of Israel

[73] Assignee: Teva Pharmaceutical Industries, Ltd., Jerusalem, Israel

[21] Appl. No.: 310,480

[22] Filed: Sep. 22, 1994

Related U.S. Application Data

[63] Continuation of Ser. No. 961,132, Oct. 14, 1992, abandoned.

[30] Foreign Application Priority Data

Oct. 16, 1991 [IL] Israel ............................ 99759

[51] Int. Cl.⁶ ..................... A61K 31/135; C07C 211/42
[52] U.S. Cl. ............................. 514/657; 564/428
[58] Field of Search ................. 564/428; 514/657

[56] References Cited

U.S. PATENT DOCUMENTS

| | | | |
|---|---|---|---|
| 3,201,470 | 8/1965 | Huebner | 260/557 |
| 3,253,037 | 5/1966 | Huebner | 260/557 |
| 3,513,244 | 5/1970 | Gittos et al. | 424/320 |

FOREIGN PATENT DOCUMENTS

| | | |
|---|---|---|
| 0436492 | 7/1991 | European Pat. Off. |
| 1033686 | 9/1965 | United Kingdom |
| 8505617 | 12/1985 | WIPO |
| WO90/01928 | 3/1990 | WIPO |

OTHER PUBLICATIONS

Youdim et al., *Progress in Medicinal Chemistry*, vol. 21, pp. 138–167 (1984).
Youdim et al., *Handbook of Experimental Pharmacology*, vol. 90, Chapter 3 (1988).
Elsworth et al., *Psychopharmacology*, vol. 57, pp. 33–38 (1978).
Birkmayer & Riederer, *Parkinson's Disease*, pp. 138–149 (1983).
Tariot et al., *Psychopharmacology*, vol. 91, pp. 489–495 (1987).
J. Mendlewicz and M. B. H. Youdim, *Brit. J. Psychiat.*, vol. 142, pp. 508–511 (1983).

*Primary Examiner*—Richard L. Raymond
*Attorney, Agent, or Firm*—John P. White

[57] ABSTRACT

N-propargyl-1-amonoindan monofluorinated in the phenyl ring and their use as selective inhibitors of monoamine oxidase (MAO).

There are provided several processes for the preparation of these novel compounds. There are also provided as novel compounds 1-aminoindans monofluorinated in the phenyl ring, which serve as intermediates in the preparation of the corresponding novel N-propargyl derivatives.

18 Claims, No Drawings

MONOFLUORINATED DERIVATIVES OF N-PROPARGYL-1-AMINOINDAN AND THEIR USE AS INHIBITORS OF MONOAMINE OXIDASE

This is a continuation of U.S. Ser. No. 07/961,132, filed Oct. 14, 1992, abandoned.

FIELD OF THE INVENTION

The present invention is in the field of selective irreversible inhibitors of the enzyme monoamine oxidase (hereinafter MAO) and relates to novel propargylamine compounds which are selective irreversible inhibitors of the B-form of the monoamine oxidase enzyme (hereinafter, MAO-B). The invention also relates to pharmaceutical compositions containing these propargylamine compounds which are particularly useful for the treatment of Parkinson's disease, memory disorders and dementia of the Alzheimer type (DAT), depression, and hyperactive syndrome in children.

BACKGROUND OF THE INVENTION AND PRIOR ART

Parkinson's disease is widely considered to be the result of degradation of the pre-synaptic dopaminergic neurons in the brain, with a subsequent decrease in the amount of the neurotransmitter dopamine, that is being released. Inadequate dopamine release, therefore, leads to the onset of voluntary muscle control disturbances symptomatic of Parkinson's disease.

Various procedures for treating Parkinson's disease have been established and are currently in widespread use, for example, the administration of L-Dopa, which is a precursor of dopamine, together with a decarboxylase inhibitor, such as L-carbidopa or benzerazide. The decarboxylase inhibitor protects the L-Dopa molecule from peripheral decarboxylation and thus ensures L-Dopa uptake by the remaining dopaminergic neurons in the striatum of the brain. Here the L-Dopa is converted into dopamine resulting in increased levels of dopamine in these neurons. In response to physiological impulses these neurons are therefore capable of releasing larger amounts of dopamine, the quantity of which approximates the normal required levels. This treatment therefore alleviates the symptoms of the disease and contributes to the well-being of the patients.

However, this L-Dopa treatment has its drawbacks, the main one being that its effectiveness is optimal only in the first few years following the onset of treatment. After this initial period the clinical response is diminished and is accompanied by adverse side effects which include dyskinesia, fluctuation in efficacy throughout the day "on-off effect") and psychiatric symptoms such as confusional states, paranoia and hallucinations. This fall-off in the effect of L-Dopa treatment is attributed to a number of factors, including the natural progression of the disease, alteration in dopamine receptors as a consequence of increased dopamine production or increased levels of dopamine metabolites, and pharmacokinetic problems of L-Dopa absorption (reviewed by Youdim et at., Progress in Medicinal Chemistry, Vol. 21, Chapter 4, pp. 138–167 (1984), Eds. Ellis and West, Elsevier, Amsterdam).

In order to overcome the drawbacks of the L-Dopa treatment, various treatments have been devised in which L-Dopa is combined with MAO inhibitors, with the aim of reducing the metabolic breakdown of the newly formed dopamine (see for example, U.S. Pat. No. 4,826,875).

MAO exists in two forms known as MAO-A and MAO-B which have selectivity for different substrates and inhibitors. For example, MAO-B metabolizes more efficiently substrates such as 2-phenylethylamine and is selectively and irreversibly inhibited by (–)-deprenyl (as described below).

It should be noted, however, that combining L-Dopa with an inhibitor of both MAO-A and MAO-B is undesirable leading to adverse side effects related to an increased level of catecholamines throughout the neuraxis. Furthermore, complete inhibition of MAO is also undesirable as it potentiates the action of sympathomimetic amines such as tyramine leading to the so-called "cheese effect" (reviewed by Youdim et al., Handbook of Experimental Pharmacology, Vol. 90, Chap. 3 (1988) Eds, Trendelenburg and Weiner, Springer-Verlag). As MAO-B was shown to be the predominant form of MAO in the brain, selective inhibitors for this form were thus considered to be a possible way for achieving a decrease in dopamine breakdown on the one hand, together with a minimization of the systemic effects of total MAO inhibition, on the other.

One of these selective MAO-B inhibitors, (–)-deprenyl, has been extensively studied and has been used as an MAO-B inhibitor to augment L-Dopa treatment. This treatment with (–)-deprenyl is generally favourable, not causing the "cheese effect" at doses causing nearly complete inhibition of MAO-B (Elsworth et al., Physchopharmacology, 57, 33 (1978). Furthermore, addition of (–)-deprenyl to a combination of L-Dopa and decarboxylase inhibitor to Parkinson's patients leads to improvements in akinesia and overall functional capacity as well as the elimination of "on-off" type fluctuations (reviewed by Birkmayer & Riederer in "Parkinson's Disease" pp. 138–149, Springer-Verlag (1983)).

Thus, (–)-deprenyl enhances and prolongs the effect of L-Dopa and permits a lowering of the dosage of L-Dopa whereby the adverse effects of L-Dopa treatment are limited.

A more potent selective inhibitor of MAO-B than the racemic mixture is the optical isomer R-(+)-N-propargyl-1-aminoindan. HCl [R-(+)-PAI.HCl] which is more selective in vivo and in vitro as described in our copending Israel Patent Application No. 92952.

However it is highly desirable to further increase the selectivity of MAO inhibitor, inhibiting preferably MAO-B and not MAO-A, thus minimizing the side effects caused by the inhibition of MAO-A.

The compounds of the present invention were found to have a surprisingly high degree of selectivity in vitro, inhibiting preferably MAO-B over MAO-A.

The compounds of the present invention are mono-fluoro derivatives of N-propargyl-1-aminoindan stereoisomers and salts thereof.

U.S. Pat. No. 3,513,244 claims generically and specifically a large number of secondary and tertiary aminoindans which are stated to have hypotensive activity. There is no disclosure of the specific compounds of the present invention, and there is no evidence that the mono-fluorinated derivatives of 1-propargylaminoindan of the present invention have ever been synthesised and characterised. Furthermore, the secondary and tertiary aminoindans of U.S. Pat. No. 3,513,244 are stated to have hypotensive activity and there is no teaching that any components of the group have any as MAO-B inhibitor activity.

British Patent No. 1,003,686 discloses a group of benzocycloalkane compounds in which the cycloalkane has from five to seven ring members and is substituted by an N-(alkynylalkyl)amino group. This patent mentioned the possibility of substituting the aromatic portion of the benzocycloalkane ring system by one or more halogen atoms. Although the compounds of the present invention are generically included in the group, they are not specifically disclosed. The compounds claimed in British Patent No. 1,003,683 are stated to be monoamine oxidase inhibitors in general, but there is no disclosure of any activity by which MAO-B is inhibited, selectively in preference over MAO-A.

The mono-fluorinated N-propargyl-1-aminoindans of the present invention are surprisingly more potent selective MAO-B inhibitors than any of the other species of the groups disclosed in both U.S. Pat. No. 3,513,244 and British Patent No. 1,003,686, enabling the inhibition of MAO-B at lower concentrations. This high potency and selectivity in vivo is a unique and surprising property of the mono-fluorinated N-propargyl-1-aminoindan compounds and their salts according to the invention, not shared by other halogenated N-propargyl-1-aminoindans.

The MAO-B inhibitors of the present invention can also be used for the treatment of patients with dementia of the Alzheimer type (DAT), and the treatment of patients with depression and for treatment of hyperactive syndrome in children. Other MAO-B inhibitors have been used in the past for the treatment of patients suffering from these diseases (Tariot et al., Psychopharmacology, 91, 489–495, 1987), J. Mendlewich and M. B. H. Youdim (Brit. J. Psychiat., 142, 508–511, 1983, Perenyi A., et al., PCT/HU89/00044, 17 Aug. 1988).

DETAILED DESCRIPTION OF THE INVENTION

The present invention provides novel mono-fluorinated derivatives of 1-propargyl aminoindans of the formula

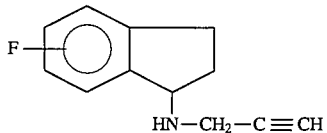

(I)

and pharmaceutically acceptable addition salts thereof.

The compounds of formula (I) may be racemic mixtures or optically pure enantiomers. Specific compounds of use in the present invention include
4-fluoro-N-propargyl-1-aminoindan
5-fluoro-N-propargyl-1-aminoindan
6-fluoro-N-propargyl-1-aminoindan
and optically pure enantiomers thereof.

A preferred compound of the invention is 6-fluoro-N-propargyl-1-aminoindan and a particularly preferred compound is the enantiomer (+)-6-fluoro-N-propargyl-1-aminoindan.

The present invention also relates to pharmaceutical compositions comprising compounds of formula (I) together with pharmaceutically acceptable carriers and/or excipients and/or diluents. The pharmaceutical compositions may be adapted for oral, rectal, parenteral, topical or transdermal administration. Suitable forms for oral administration include tablets, compressed or coated pills, dragees, sachets, hard or soft gelating capsules, syrups and suspensions. Suitable forms for parenteral administration include ampoules or vials which additionally contain an aqueous or nonaqueous solution or emulsion. Compositions adapted for rectal administration include suppositories with hydrophilic and/or hydrophobic vehicles.

The pharmaceutical compositions may be in dosage unit forms preferably containing 1–20 mg of the compound according to formula (I). The pharmaceutical compositions may additionally comprise levodopa and a decarboxylase inhibitor, such as L-carbidopa or benzerazide. Preferably the pharmaceutical composition will comprise 1–20 mg of the compound according to formula (I), 50–250 mg levodopa and 10–25 mg of L-carbidopa. Another preferable pharmaceutical composition will comprise 2–10 mg of the compound according to formula (I), 50–250 mg levodopa and 12.5–50 mg benzerazide.

The present invention further relates to the use of the compound of formula (I) for manufacturing a pharmaceutical composition for the treatment of human patients suffering from Parkinson's disease, memory disorders, dementia of the Alzheimer type and hyperactive syndrome in children.

Another aspect of the present invention relates to methods of treatment of human patients suffering from Parkinson's disease, memory disorders, dementia of the Alzheimer type and hyperactive syndrome comprising administering a therapeutically effective amount of a compound according to formula (I) or a pharmaceutically acceptable addition salt thereof.

The invention also relates to processes for the preparation of the compound of formula (I). The racemic mixture of the compound of formula (I) can be prepared by reacting aryl fluorinated 1-chloro or 1-bromoindans, with propargylamine. Alternatively, these racemates may be prepared by reacting propargylamine with substituted 1-indanones to form the corresponding imines, followed by reduction of the carbon-nitrogen double bond of the imine with a suitable agent, such as sodium borohydride. Another method of preparation of the racemic mixture of the compound of formula (I) comprises the reaction of a racemic fluorinated 1-aminoindan of the formula:

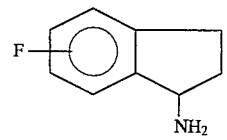

(II)

with propargyl bromide or propargyl chloride in the presence of an organic or inorganic base, optionally in the presence of a suitable solvent and, if desired, converting the resulting free base of formula I into a pharmaceutically acceptable acid addition salt thereof.

The racemic mixture of (+) and (−) enantiomers of fluorinated 1-aminoindan may be prepared by chemical reduction of corresponding fluorinated oximes, e.g., with Zn in acetic acid or by catalytic hydrogenation. Fluorinated indan-1-one may be prepared, e.g., by Friedel-Crafts cyclization of fluorinated dihydrocinnamic chloride using aluminium chloride or other Lewis acids as condensing agents. Fluorinated dihydrocinnamic chlorides may be prepared also.

The enantiomers of the compounds of formula (I) may be obtained by optical resolution of racemic mixtures of (+) and (−) enantiomers of compounds of formula (I). Such a resolution can be accomplished by conventional resolution methods, well known to a person skilled in the art, such as those described in "Enantiomers, Racemates and Resolutions" by J. Jacques, A. Collet and S. Willen, Pub. John Wiley & Sons, New York 1981. For example, the resolution may be carried out by preparative chromatography on a chiral column. Another suitable resolution method is the formation of diastereomeric salts with a chiral acid such as tartaric, maleic, and mandelic acid or N-acetyl derivatives of amino acids, such as N-acetyl leucine, followed by recrystallization to isolate the diastereomeric salt of the desired enantiomer.

In accordance with this invention, the (+) enantiomers of the compounds of formula (I) can be prepared directly from the optically active (–)-enantiomers of fluorinated 1-aminoindans of the formula

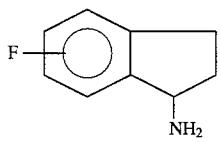

(II)

by reaction with propargyl bromide or propargyl chloride in the presence of an organic or inorganic base and optionally in the presence of a suitable solvent and if desired converting the resulting (–) enantiomeric free base of formula I into a pharmaceutically acceptable acid salt thereof.

Suitable organic or inorganic bases for use in the above reaction are, e.g., triethylamine, pyridine, alkali metal carbonates or bicarbonates etc. If the reaction is conducted in the presence of a solvent, this may be chosen from, e.g., toluene, methylene chloride and acetonitrile. A preferred method of preparation of the aforementioned compounds is the reaction between fluorinated (–)-1-aminoindans with propargyl chloride using potassium carbonate as a base and acetonitrile as solvent.

The above described reaction between fluorinated 1-aminoindans generally results in a mixture of unreacted primary amines, the desired secondary amines and tertiary amines, namely the N,N-bispropargylamino products. The desired secondary amines, i.e. fluorinated N-propargyl-1-aminoindans, can be separated by conventional separation methods including but not limited to chromatography, distillation and selective extraction.

The compounds of formula (II) herein as well as their acid addition salts are novel. These compounds, which are intermediates in the preparation of compounds of formula (I) herein, are provided as racemates and as (–) enantiomers.

Alternatively, the fluorinated (–)-1-aminoindans may be prepared by reacting fluorinated 1-indanone with an optically active amine, followed by reduction of the carbon-nitrogen double bond of the resulting imine by hydrogenation over a suitable catalyst such as platinum oxide, Raney nickel, or by chemical reduction, for example, with sodium borohydride. Suitable optically active amines are, for example, one of the antipodes of alpha-phenylethylamine or an ester of an amino acid, such as phenylalanine. The benzylic N—C bond may be cleaved by hydrogenolysis.

Halogenated (–) aminoindans may also be prepared by enzyme mediated selective acylation of a racemic mixture of a compound of the formula:

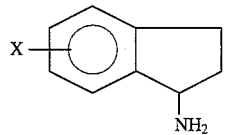

(III)

preferably using the enzyme subtilisin A isolated from Bacillus licheniformis in 3-methyl-3-pentanol with trifluoroethyl butyrate as the acylating agent, thereby forming a mixture comprising an acylated (+) enantiomer fluoro-1-aminoindan and a non-acylated (–) enantiomer of fluoro-1-aminoindan. The resulting halogenated (–)-1-aminoindan may be readily separated from the corresponding (+)-amide by chromatography, distillation, selective extraction, or conversion of the free base into a suitable acid addition salt and its recrystallisation.

Finally the (+)-fluoro-N-propargyl-1-aminoindan is prepared by reacting the separated (–) fluoro-1-aminoindan with propargyl bromide or propargyl chloride in the presence of an organic or inorganic base, optionally in the presence of a suitable solvent, and isolating the (+) fluoro-N-propargyl-1-aminoindan formed as the free base or a pharmaceutically acceptable acid addition salt thereof.

Additional methods for preparing fluorinated (–)-1-aminoindans are the reduction, as described above, of indan-1-one oxime ethers, wherein the alkyl portions of the ether contains an optically pure chiral centre. Alternatively, a non-chiral derivative of fluorinated indan-1-ones containing a carbon-nitrogen double bond, such as an imine or oxime, can be reduced with a chiral reducing agent, e.g., a complex of lithium aluminium hydride and ephedrine.

Pharmaceutically acceptable acid addition salts of the compounds of the present invention may be prepared by reacting according to conventional methods the free base forms of the compounds of formula (I) with the desired acids in the presence of a suitable solvent. Similarly, an acid addition salt may be converted to the free base form or directly to another acid addition salt by methods well known to those skilled in the art.

Thus, the present invention also provides a method for the preparation of a (–) enantiomer of the formula (III) wherein X represents a halogen, comprising:

a) selectively acylating a racemic mixture of a compound of the formula (III) wherein X represents a halogen, using the enzyme subtilisin A isolated from Bacillus licheniformis to form a mixture comprising an acylated (+) enantiomer of halogenated-1-aminoindan and a non-acylated (–) enantiomer of halogenated-1-aminoindan, b) separating the (–) halogenated-1-aminoindan from the acylated (+) halogenated-1-aminoindan by chromatography, distillation, selective extraction or conversion of the free base into a suitable acid addition salt and its recrystallization.

DESCRIPTION OF SPECIFIC EMBODIMENTS

The present invention will not be specifically described in the following Examples to which it is not limited.

EXAMPLE 1

5-Fluoro-1-aminoindan

A solution of 3-fluorobenzaldehyde (10 g), malonic acid (15.6 g) and piperidine (0.7 ml) in pyridine (35 ml) was heated at reflux for 3.5 hours. After cooling to room temperature, the reaction mixture was added to a mixture of ice water (210 ml) and conc. hydrochloric acid (56 ml). The precipitate was isolated by filtration and recrystallized from methanol/water to give 3-fluorocinnamic acid (11.3 g).

A mixture of 3-fluorocinnamic acid (11 g), sodium hydroxide (2.7 g), 3% sodium amalgam (220 g) in 340 ml of water was heated overnight at 70°–80° C. The aqueous solution was decanted from the mercury residue and acidified with conc. hydrochloric acid (35 ml) to pH 2, cooled at 0° C. and the resulting precipitated 3-fluorohydrocinnamic acid (10 g) isolated by filtration.

A solution of 3-fluorohydrocinnamic acid (28 g) in thionyl chloride (90 ml) was heated at reflux for 3 hours. 3-Fluorohydrocinnamoyl chloride (27 g) was isolated by distillation (150°–110° C. @ ca 20 mm.Hg).

A solution of 3-fluorodihydrocinnamoyl chloride (15.4 g) in carbon disulfide (78 ml) was added dropwise to a cold (–5° C.) mixture of aluminium chloride (13.9 g) in carbon disulfide (300 ml) for 30 minutes. During this time and for 30 minutes the mixture was allowed to warm to room temperature (1 hr), then it was heated to reflux (1 hr) and finally the volatiles were removed by distillation under reduced pressure. The residue was dissolved in methylene chloride (400 ml) and washed successively with 10% aqueous sodium hydroxide and water. After drying (magnesium sulfate) and solvent removal in vacuo, 5-fluoroindanone (2 g) was isolated by recrystallisation from hexane.

A solution of 5-fluoroindanone (10 g), hydroxylamine hydrochloride (9 g), potassium carbonate (23 g) and water (3.5 ml) in 96% ethanol (40 ml) was heated to reflux, cooled to ca 45 and additional hydroxylamine hydrochloride (4.5 g) and potassium carbonate (11.5 g) were added and refluxed for an additional 30 min. At this time the mixture was poured into cold water (300 ml) and stirred in an ice bath for one hour; 5-fluoroindanone oxime (9.8 g) was isolated by filtration.

Zinc powder (20.2 g) was added during three hours to the stirred solution of the above oxime (20.2 g) in acetic acid (200 ml) which maintains the temperature at 25°–35° C. The resulting mixture was stirred an additional 12 hours at room temperature. The solids were removed by filtration and the filtrate concentrated in vacuo. The concentrated filtrate was partitioned between water and toluene and the aqueous phase adjusted to pH 12 with ammonium hydroxide and extracted with toluene. Solvent removal in vacuo gave 5-fluoro-1-aminoindan (17.8 g) as a colored oil.

IR: 690, 748, 815, 864, 929, 1126, 1244, 1315, 1377, 1433, 1454, 1485, 1595, 1614, 2800, 3000, 3300 cm$^{-1}$. NMR: 1.81, 2.4, 2.8, 6.8, 7.2; m/e 151.0786 C$_9$H$_{10}$NF;

EXAMPLE 2

4-fluoro-1-aminoindan

The title compound was prepared in 47% overall yield according to the procedure of Example 1 except that 2-fluorobenzaldehyde was used instead of 3-fluorobenzaldehyde.

IR: 708, 780, 1170, 1242, 1290, 1377, 1472, 1587, 1624, 2800, 2950, 3200 cm$^{-1}$; NMR: 1.7, 2.1, 2.7, 2.9, 3.1, 4.3, 6.8, 7.0, 7.1; m/e: 151.0782 (C$_9$H$_{10}$NF)

EXAMPLE 3

6-fluoro-1-aminoindan

The title compound was prepared in 29% overall yield according to the procedure of Example 1 except that 4-fluorobenzaldehyde was used instead of 3-fluorobenzaldehyde.

IR: 694, 740, 770, 812, 844, 870, 912, 1130, 1163, 1253, 1441, 1483, 1597, 1612, 2800, 3000, 3300 cm$^{-1}$; NMR: 1.5, 2.1, 2.8, 6.8, 7.1; m/e 151.0774 C$_9$H$_{10}$NF

EXAMPLE 4

(−)-6-Fluoro-1-aminoindan

A solution of 6-fluoro-1-aminoindan (4,2 g) in methanol (10 ml) was added to a heated clear solution of L-N-acetyl-methyl-3,4-dimethoxyphenylalanine (7,8 g) in methanol (30 ml). The mixture was stirred with cooling. The product was crystallized from methanol with carbon black (0.5 g) two times and checked by HPLC (chiral column).

The title compound was obtained by extraction from aqueous 10% sodium hydroxide with methylene chloride, drying and evaporation.

$[\alpha]_D$ −7.9° C. (c 2%, EtOH).

The spectral properties were identical to the compound of Example 3.

EXAMPLE 5

(+)-6-Fluoro-1-aminoindan

The title compound was crystallized from mother liquors after separation of (−)-antipode by the procedure of Example 4, and repeated crystallization from the same solvent. The title compound was obtained by extraction from aqueous 10% sodium hydroxide with methylene chloride, drying and evaporation. The spectral properties were identical to the compound of Example 3.

EXAMPLE 6

(−)-4-Fluoro-1-aminoindan

The title compound was prepared in 50% yield according to the procedure of Example 4 except that 4-fluoro-1-aminoindan was used instead of 6-fluoro-1-aminoindan. The spectral properties were identical to the compound of Example 2.

EXAMPLE 7

(−)-5-Fluoro-1-aminoindan

The title compound was prepared in 25% yield according to the procedure of Example 4 except that 5-fluoro-1-aminoindan was used instead of 6-fluoro-1-aminoindan. The spectral properties were identical to the compound of Example 1.

EXAMPLE 8

(−)-6-Fluoro-1-aminoindan

A solution of 20 grams of racemic 6-fluoro-1-aminoindan and 60 ml of trifluoroethyl butyrate in 400 ml of 3-methyl-3-pentanol was treated with 2 g of subtilisin A. The resulting suspension was shaken on an orbital shaker at 200 rpm at 40° C. for 72 hours at which time the enzyme was removed by filtration, and the filtrate was extracted with 1M aqueous hydrochloric acid. The aqueous layer was back extracted with methylene chloride and freeze dried to yield 10 grams of the title compound as the HCl salt. The free base was obtained by suspending the HCl salt in aqueous 10% sodium hydroxide, extracting with methylene chloride, drying and evaporation. The free base so obtained was of 99% optical purity with spectroscopic properties identical to those of the compound from Example 4.

EXAMPLE 9

(−)-5-Fluoro-1-aminoindan

The title compound was obtained in 99% optical purity by the method of Example 8 using racemic 5-fluoro-1-aminoindan instead of 6-fluoro-1-aminoindan.

EXAMPLE 10

(−)-4-Fluoro-1-aminoindan

The title compound was obtained in 99% optical purity by the method of Example 8 using racemic 4-fluoro-1-aminoindan instead of 6-fluoro-1-aminoindan.

EXAMPLE 11

5-Fluoro-N-propargyl-1-aminoindan hydrochloride

A mixture of 5-fluoro-1-aminoindan (6.2 g), potassium carbonate (7.4 g) and acetonitrile (54 ml) was heated under nitrogen to 60° C. Propargyl chloride (3.3 g) was added and heating was continued overnight. Acetonitrile was evaporated and products were distributed between methylene chloride and 10% sodium hydroxide in water.

The free base of the title compound was isolated by flash column chromatography on silica gel.

An ethereal solution of this base was treated with hydrogen chloride gas and the title compound (2.8 g) was isolated by filtration.

M.p. 178.4° C. (decomp.); IR (KBr) 899, 1216, 1437, 1491, 2359, 2928, 3287 cm$^{-1}$. Anal. calcd. for $C_{12}H_{15}ClFN$: % C 63.86, H 5.81, N 6.21, Cl 15.71; found % C 63.38, H. 5.69, N 6.33, Cl 15.00.

EXAMPLE 12

4-Fluoro-N-propargyl-1-aminoindan hydrochloride

The title compound was prepared in 29% yield according to the procedure of Example 11 except that 4-fluoro-1-aminoindan was used instead of 5-fluoro-1-aminoindan.

M.p. 191.3° C. (decomp.); IR (KBr) 771, 1045, 1248 1473, 1586, 2400, 2653, 2719, 2949, 3200 cm$^{-1}$; m/e 190. Anal. calcd. for $C_{12}H_{15}ClFN$; % C 63.86, H 5.81, N 6.21, Cl 15.71; found % C 63.66, H.58, N 6.15, Cl 15.54.

EXAMPLE 13

6-Fluoro-1-propargylaminoindan

The title compound was prepared in 44% yield according to the procedure of Example 11 except that 6-fluoro-1-aminoindan was used instead of 5-fluoro-1-aminoindan. The spectral properties were identical to the compound of Example 16.

EXAMPLE 14

(+)-4-Fluoro-N-propargyl-1-aminoindan hydrochloride

The title compound was prepared in 70% yield according to the procedure of Example 11 except that (−)-4-fluoro-1-aminoindan was used instead of 5-fluoro-1-aminoindan.

M.p. 218.9° C. (decomp.); $[\alpha]D+10.7$ (c, 0.4%, $H_2O$); NMR ($D_2O$) 2.35 m, 2.65 m, 3.00 m, 3.93 s, 4.8 s, 5.00 m, 7.15 m, 7.33 m ppm; m/e 189.09; IR (KBr) 771, 1248, 1583, 2438, 2655, 2718, 2849, 2945, 3239 cm$^{-1}$; Anal. calcd. for $C_{12}H_{15}ClFN$: % C 63.86, H. 5.81, N. 6.21, Cl 15.71; found % C 64.01, H 5.74, N 6.05, Cl 15.80.

EXAMPLE 15

(+)-5-Fluoro-N-propargyl-1-aminoindan hydrochloride

The title compound was prepared in 50% yield according to the procedure of Example 11 except that (−)-5-fluoro-1-aminoindan was used instead of 5-fluoro-1-aminoindan.

NMR ($CDCl_3$) 2.35 m, 2.8 m, 3.3 m, 3.6 s, 4.6 d, 6.8 m, 7.6 m ppm; m/e 189.09; IR (KBr) 690, 713, 833, 945, 1016, 1238, 1252, 1420, 1444, 1487, 1600, 1625, 2100, 2400, 2500, 2900, 3250 cm$^{-1}$; $[\alpha]_D+23.5°$ (c, 0.2%, $H_2O$); M.p. 192° C. (decomp.); Anal. calcd. for $C_{12}H_{15}ClFN$; % C 63.86, H 5.81, N 6.21, Cl 15.71; found % C 64.52, H. 5.68, N 6.35, Cl 15.47.

EXAMPLE 16

(+)-6-Fluoro-N-propargyl-1-aminoindan hydrochloride

The title compound was prepared in 46% yield according to the procedure of Example 11 except that (−)-6-fluoro-1-aminoindan was used instead of 5-fluoro-1-aminoindan.

M.p. 220.8° C. (decomp.); $[\alpha]D=+18.1°$ (c, 0.3%, $H_2O$); IR (KBr) 694, 735, 820, 880, 1042, 1131, 1173, 1228, 1246, 1256, 1365, 1460, 1492, 1584, 1599, 2128, 2438, 2946, 3064, 3224 cm$^{-1}$. Anal. calcd. for $C_{12}H_{15}ClFN$: % C 63.86, H. 5.81, N 6.21, Cl 15.71; found % C 64.39, H 5.54, N. 6.21, Cl 15.71.

EXAMPLE 17

(−)-6-Fluoro-N-propargyl-1-aminoindan hydrochloride

The title compound was prepared in 61% yield according to the procedure of Example 11, except that (+)-6-fluoro-1-aminoindan was used instead of 5-fluoro-1-aminoindan.

M.p. 220° C.; $[\alpha]D=-17.7°$; $IR_1$(KBr) 828, 1130, 1228, 1493, 1597, 2440, 2633, 2945, 3229 cm$^{-1}$.

EXAMPLE 18

6-Chloro-N-propargyl-1-aminoindan hydrochloride

The title compound was prepared in 33.1% yield according to the procedure of Example 11 except that 6-chloro-1-aminoindan was used instead of 5-fluoro-1-aminoindan.

M.p. 191.7° C. (decomp.); NMR ($D_2O$) 2.3 m, 2.5 m, 3.1 m, 3.93 s, 4.9 d, 5 m ppm; m/e 205.0658 and 207.0640. IR (KBr) 760, 812, 1091, 1259, 1472, 1578, 1599, 1651, 1700, 2900, 3300 cm$^{-1}$; Anal. calcd. for $C_{12}H_{13}NCl_2$: % C 59.52, H 5.41, N 5.78, Cl 29.28; found % C 59.80, H 5.33, N 5.61, Cl 29.11.

EXAMPLE 19

4,6-Difluoro-N-propargyl-1-aminoindan hydrochloride

The title compound was prepared in 61.8% yield according to the procedure of Example 11 except that 4,6-difluoro-1-aminoindan was used instead of 5-fluoro-1-aminoindan.

M.P. 218.8° C. (decomp.); NMR ($D_2O$) 1.16, 2.36 m, 2.63 m, 3.02 m, 3.98 s, 7.01 s, 7.18 d; m/e 207.0817; IR (KBr) 851, 872, 980, 995, 1055, 1113, 1335, 1447, 1462, 1487, 1584, 1601, 1630, 2400, 2700, 2950, 320 cm$^{-1}$; Anal. calcd. for $C_{12}H_{12}NClF_2$; % C 59.15, H 4.96, N 5.75, Cl 14.55; found % C 59.41, H 5.19, N 5.61, Cl 13.98.

EXAMPLE 20

Pharmaceutical formulation

A typical pharmaceutical preparation can be prepared as follows:

Each tablet contains:

| | |
|---|---|
| 6-fluoro-N-propargylaminoindan hydrochloride | 3.0 mg |
| Pregelatinized starch | 11.0 mg |
| Starch | 48.5 mg |
| Microcrystalline cellulose | 80.0 mg |
| Ethylcellulose | 1.0 mg |
| Talc | 1.5 mg |
| Tablet weight: | 145.0 mg |

Blend the excipients and the active granulate with isopropyl alcohol. Dry the mixture, blend with the talc and compress into tablets.

Similar formulations can be prepared by one skilled in the art for each of the compounds of the invention.

EXAMPLE 21

Tablet Composition

Each tablet contains:

| | |
|---|---|
| 6-fluoro-N-propargyl-1-aminoindan-hydrochloride | 5.0 mg |
| Levodopa | 100.0 mg |
| Carbidopa | 25.0 mg |
| Pregelatinised starch | 24.0 mg |
| Starch | 40.0 mg |
| Microcrystalline cellulose | 49.5 mg |

Similar formulations can be prepared by one skilled in the art for each of the compounds of the invention.

EXAMPLE 22

Inhibition of MAO Activity In-Vitro
Experimental Protocol:

These experiments were performed essentially according to the protocol of K. F. Tipton and M. B. H. Youdim in CIBA Symposium No. 39, Editors: G. E. W. Wolstenholme and J. Knight, Elsevier, Amsterdam, 1976, pp. 393–403. The MAO enzyme source was a homogenate of rat brain in 0.3M sucrose which was centrifuged at 600 g for 15 minutes. The supernatant was diluted appropriately in 0.05M phosphate buffer and preincubated with serial dilutions of compounds of interest which are listed below for 20 minutes at 37° C. $^{14}$C-labeled substrates (2-phenylethylamine, hereinafter PEA; 5-hydroxytryptamine, hereinafter 5-HT) were then added and the incubation continued for a further 20 minutes (PEA) or 30–45 minutes (5-HT). Substrate concentrations used were 20 µM (PEA) or 1 mM (5-HT). In the case of PEA the enzyme concentration was chosen so that not more than 10% of the substrate was metabolized during the course of the reaction. The reaction was then stopped by the addition of tranylcypromine (to final concentration of 1 mM) and the incubate filtered over a small column of Amberlite CG-50; buffered to pH 6.3. The column was washed with 1.5 ml water, the eluates pooled and the radioactive content determined by liquid scintillation spectrometry. Since the amine substrates are totally retained on the column, radioactivity in the eluate indicates the production of neutral and acidic metabolites formed as a result of MAO activity. Activity of MAO in the sample was expressed as a percentage of control activity in the absence of inhibitors after subtraction of appropriate blank values. The activity determined using PEA as a substrate is referred to as MAO B activity, and that determined using 5-HT as a substrate is referred to as MAO A activity. The inhibitory activity of each of the compounds was examined separately in vitro and is shown in Table 1.

The results shown in Table 1 demonstrate that the fluorinated propargylaminoindans of the invention are surprisingly more selective MAO-B inhibitors than the non-halogenated parent compound. The preferred compound of the invention, (+)-6-F-propargyl-N-aminoindan is much more selective than the parent non-fluorinated compound and more selective than the other fluorinated derivatives.

TABLE 1

IC$_{50}$ Values (µM) for Inhibition of MAO-A and MAO-B in Brain Homogenates

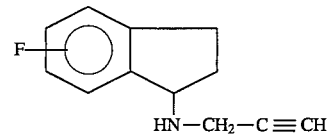

HN—CH$_2$—C≡CH

| Compound Substituent | MAO-B | MAO-A | Selectivity MAO-A/MAO-B |
|---|---|---|---|
| 4-F | 0.0058 | 0.5 | 86 |
| (+)-4-F | 0.0052 | 0.34 | 65 |
| 5-F | 0.006 | 0.7 | 116 |
| (+)-5-F | 0.0057 | 0.14 | 24 |
| 6-F | 0.0062 | 4.00 | 645 |
| (+)-6-F | 0.00022 | 2.8 | 1244 |
| (−)-6-F | 12 | 40 | 3 |
| 6-Cl | 0.0077 | 6.9 | 896 |
| (+)-4,6-Difluoro | 0.5 | 0.8 | 2 |
| H | 0.003 | 0.073 | 24 |

IC$_{50}$ the concentration that caused 50% inhibition in MAO activity

EXAMPLE 23

Inhibition of MAO Activity Ex-vivo: Acute Treatment
Experimental Protocol:

Rats (male Sprague-Dawley derived) weighing 250±20 g were treated with the desired compound by intraperitoneal injection (ip) or oral gavage (po) and decapitated 2 hours later. Groups of three rats were used for each dose level of the compound and MAO activity was determined in the brain and liver using the general technique described above. The amount of protein in each incubation was determined using the Folin-Lowry method, and enzyme activity was calculated as nmol substrate metabolized per hour incubation for each mg protein. Activity of MAO in tissues from animals treated with inhibitors was expressed as a percentage of the enzyme activity in a group of control animals which were administered the vehicle alone (water in the case of oral gavage, or 0.9% saline in the case of intraperitoneal injection) and killed as above. The results are presented in Table 2.

The ex-vivo experiment demonstrates that the monofluorinated derivates of 1-propargylaminoindan of the present invention are more potent and selective in the inhibition of MAO-B as compared to MAO-A than the 6-chloro derivates.

TABLE 2

Ex-vivo MAO Inhibitory Activity

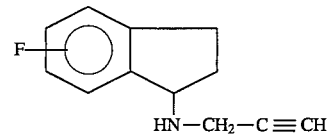

HN—CH$_2$—C≡CH

| Compound Substituent R | ED-50 BRAIN (mg/kg) | | | ED-50 LIVER (mg/kg) | | |
|---|---|---|---|---|---|---|
| | MAO-B | MAO-A | MAO-A/MAO-B | MAO-B | MAO-A | MAO-A/MAO-B |
| 4-F | 0.22 | 1.4 | 6 | 0.13 | 2.4 | 18.5 |
| (+)-4-F | 0.33 | >1.0 | >3 | 0.17 | >1.0 | >5.9 |
| 5-F | 0.4 | 2.3 | 6 | 0.06 | 2.2 | 36.7 |
| (+)-5-F | 0.07 | >0.1 | >1.4 | 0.07 | >0.1 | >1.4 |
| 6-F | 0.13 | 22 | 170 | ND | ND | ND |
| (+)-6-F | 0.14 | 21.3 | 152 | 0.13 | 5.2 | 40 |
| (−)-6-F | 0.45 | 23 | 51 | <0.5 | ND | ND |
| 6-Cl | 1.7 | 10 | 5.8 | ND | ND | ND |
| (+)4,6-Difluoro | 3.7 | 2.9 | 1 | ND | ND | ND |
| H | 0.07 | 1.2 | 17 | 0.06 | 5 | 83 |

ND - Not determined
ED-50 - The effective (mg/kg) that caused 50% inhibition in MAO activity
MAO-A/MAO-B - This is a measure of selectivity

EXAMPLE 24

Tyramine Potentiation in Vivo
Experimental protocol:

Male rats weighing 310±20 gr (5–10 per group) were treated with the desired compound by oral administration (gavage) of 5 mg/kg.

On the previous day a tail artery cannulation was performed to enable direct blood pressure measurements. On the experimental day the cannulae were connected to pressure transducers. The animals were unrestrained and were kept in a glass sided open top tank during the pressure measurements. Tyramine was administered orally by gavage in increasing doses (5,10 and 20 mg/kg), allowing 30 minutes between doses. The desired compound was administered 30 minutes after the last dose of tyramine. Tyramine was administered again, in increasing doses, as described above, one hour after the desired compound was administered. Tyramine alone caused increase of blood pressure which was potentiated by the compounds.

The tyramine potentiating effect was calculated as a ratio between the areas under the curve of blood pressure measured with tyramine alone (20 mg/kg) and that measured after administration of the desired compounds and tyramine. Results:

The results are presented in Table 3. The three fluorinated propargyl aminoindans tested caused certain potentiation of tyramine effect on blood pressure at this high dose of 5 mg/kg. (+)-6-F-N-propargyl-1-aminoindan has the lowest potentiating effect as compared to the (+)-5-F and (+)-4-F derivatives.

The results of this experiment indicate that the MAO-B selectivity of the fluorinated derivates and especially of their (+) enantiomers prevent the tyramine potentiating effect ("cheese effect") caused by the non-selective MAO-inhibitors. This tyramine potentiating effects is one of the major reasons which prevented the clinical use of non-selective MAO-inhibitors. The preferred compound in this regard is (+)-6-F-N-propargyl-1-aminoindan which does not cause significant potentiation of tyramine at a high dose of 5 mg/kg body weight. The $ED_{50}$ for brain MAO-B inhibition in rat is 0.14 mg/kg and a dose 35 times higher results practically in no tyramine potentiation, indicating the potential safety in clinical use.

TABLE 3

Potentiation of blood pressure response to tyramine

| Compound (5 mg/kg) | Potentiation of blood pressure |
| --- | --- |
| (+)-6-Fluoropropargyl-1-amonoindan | 1.2 fold |
| (+)-4-Fluoropropargyl-1-aminoindan | 1.55 fold |
| (+)-5-Fluoropropargyl-1-aminoindan | 2.25 fold |

- Compounds were administered orally
- Tyramine was administered orally, 20 mg/kg body weight

We claim:

1. A compound selected from the group consisting of 4-fluoro-N-propargyl-1-aminoindan, 5-fluoro-N-propargyl-1-aminoindan, 6-fluoro-N-propargyl-1-aminoindan and pharmaceutically acceptable addition salts thereof.

2. 4-fluoro-N-propargyl-1-aminoindan or pharmaceutically acceptable acid addition salts thereof.

3. 5-fluoro-N-propargyl-1-aminoindan or pharmaceutically acceptable acid addition salts thereof.

4. 6-fluoro-N-propargyl-1-aminoindan or pharmaceutically acceptable acid addition salts thereof.

5. An optically pure (+) enantiomer of the compound of claim 1 or pharmaceutically acceptable addition salts thereof.

6. An optically pure (−) enantiomer of the compound of claim 1 or pharmaceutically acceptable addition salts thereof.

7. An optically pure (+) enantiomer of the compound of claim 2 or pharmaceutically acceptable addition salts thereof.

8. An optically pure (+) enantiomer of the compound of claim 3 or pharmaceutically acceptable addition salts thereof.

9. An optically pure (+) enantiomer of the compound of claim 4 or pharmaceutically acceptable addition salts thereof.

10. (+)-6-fluoro-N-propargyl-1-aminodan or a pharmaceutically acceptable addition salt thereof.

11. A pharmaceutical composition comprising an effective amount of a compound according to claim 1 and a pharmaceutically acceptable carrier.

12. A pharmaceutical composition according to claim 11 for oral, rectal, parenteral, topical or transdermal administration.

13. A pharmaceutical composition according to claim 11 in dosage unit form, each dosage unit containing from 1 to 20 mg of the compound.

14. A pharmaceutical composition according to claim 11, further comprising levodopa and a decarboxylase inhibitor.

15. A pharmaceutical composition according to claim 14 in dosage unit form, wherein each dosage unit comprises 1–10 mg of the compound, 50–250 mg levodopa and 10–25 mg L-carbidopa.

16. A pharmaceutical composition according to claim 14 in dosage unit form, wherein each dosage unit comprises 1–10 mg of the compound, 50–250 mg levodopa and 12.5–50 mg benzerazide.

17. A pharmaceutical composition comprising, in combination with a pharmaceutically acceptable carrier, a compound according to claim 1 in an amount effective for the treatment of human patients suffering from Parkinson's disease, memory disorders, dementia of the Alzheimer type, depression or hyperactive syndrome in children.

18. A method of treating a human patient suffering from Parkinson's disease, memory disorders, dementia of the Alzheimer type, depression or hyperactive syndrome comprising administering to the human patient a therapeutically effective amount of a compound according to any one of claims 1 or a pharmaceutically acceptable acid addition salt thereof.

* * * * *

UNITED STATES PATENT AND TRADEMARK OFFICE
CERTIFICATE OF CORRECTION

PATENT NO. : 5,486,541
DATED : January 23, 1996
INVENTOR(S) : Jeff Sterling et al.

It is certified that error appears in the above-indentified patent and that said Letters Patent is hereby corrected as shown below:

Column 14, lines 48-49:

In claim 18, "according to any one of claims 1" should read —according to claim 1—.

Column 14, line 16:

In claim 10, "(+)-6-fluoro-N-propargyl-1-aminodan" should read --(+)-6-fluoro-N-propargyl-1-aminoindan--.

Title page, in the ABSTRACT, line 1, "N-propargyl-1-amonoindan" should read --N-propargyl-1-aminoindan--.

Signed and Sealed this

Thirteenth Day of August, 1996

Attest:

BRUCE LEHMAN

*Attesting Officer*  *Commissioner of Patents and Trademarks*